United States Patent
Kim et al.

(10) Patent No.: US 9,902,983 B2
(45) Date of Patent: Feb. 27, 2018

(54) AGAROOLIGOSACCHARIDE HYDROLASE AND METHOD FOR PRODUCING 3,6-ANHYDRO-L-GALACTOSE AND GALACTOSE FROM AGAROSE BY USING SAME

(71) Applicant: Korea University Research and Business Foundation, Seoul (KR)

(72) Inventors: Kyoung Heon Kim, Seoul (KR); In-Geol Choi, Seoul (KR); Chan Hyoung Lee, Seoul (KR); Hee Taek Kim, Jeju-do (KR); Eun-Ju Yun, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 15/029,160

(22) PCT Filed: Oct. 8, 2014

(86) PCT No.: PCT/KR2014/009470
§ 371 (c)(1),
(2) Date: Apr. 13, 2016

(87) PCT Pub. No.: WO2015/056923
PCT Pub. Date: Apr. 23, 2015

(65) Prior Publication Data
US 2016/0265012 A1  Sep. 15, 2016

(30) Foreign Application Priority Data
Oct. 14, 2013 (KR) .................. 10-2013-0121990

(51) Int. Cl.
| | |
|---|---|
| C12P 7/06 | (2006.01) |
| C12P 19/14 | (2006.01) |
| C12P 19/02 | (2006.01) |
| C12N 9/38 | (2006.01) |
| C12N 9/40 | (2006.01) |

(52) U.S. Cl.
CPC ............ *C12P 19/14* (2013.01); *C12N 9/2465* (2013.01); *C12N 9/2468* (2013.01); *C12P 19/02* (2013.01); *C12Y 302/01082* (2013.01); *C12Y 302/01* (2013.01); *C12Y 302/01081* (2013.01); *C12Y 302/01159* (2013.01)

(58) Field of Classification Search
None
See application file for complete search history.

(56) References Cited

U.S. PATENT DOCUMENTS

| | | | |
|---|---|---|---|
| 6,911,432 B2 | 6/2005 | Enoki et al. | |
| 7,622,291 B2 | 11/2009 | Tomono et al. | |

FOREIGN PATENT DOCUMENTS

KR    10-1293668 B2    8/2013

OTHER PUBLICATIONS

NCBI Accession No. WP_014232195, May 18, 3013.*
Roh et al., Journal of Bacteriology, vol. 194, pp. 2773-2774, May 2012.*
Roh et al., GenBank Accession AEX22320.1 May 2012.*
Yun et al., "Enzymatic production of 3,6-anhydro-L-galactose from agarose and its purification and in vitro skin whitening and anti-inflammatory activities," Appl Microbial Biotechnol (2013); 97:2961-2970.
Jol et al., "A Novel High-Performance Anion-Exchange Chromatographic Method for the ANalysis of Carrageenans and Agars Containing 3,6-Anhydrogalactose," Analytical Biochemistry (1999); 268:213-222.
Kim et al., "Acidity Tunable Ionic Liquids as Catalysts for Conversion of Agar into Mixed Sugars," Bull. Korean Chem. Soc. (2010) 31(2):511-514.

* cited by examiner

*Primary Examiner* — Richard G Hutson
(74) *Attorney, Agent, or Firm* — Fox Rothschild LLP

(57) ABSTRACT

The present invention relates to agarooligosaccharide hydrolase and a method for producing 3,6-anhydro-L-galactose and galactose from agarose by using the same. More specifically, the production yield of 3,6-anhydro-L-galactose and galactose from agarose, that is, the saccharification yield, is improved by using β-agarooligosaccharide hydrolase having an agarotriose hydrolytic activity.

6 Claims, 6 Drawing Sheets

[FIG. 1]
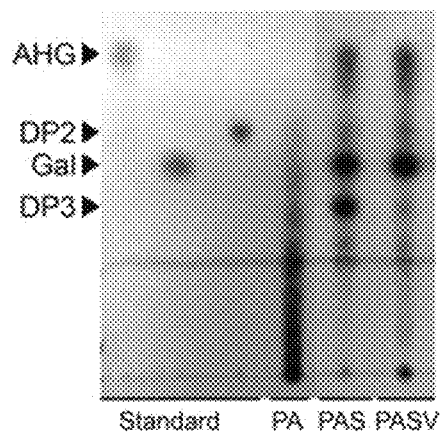
[FIG. 2]
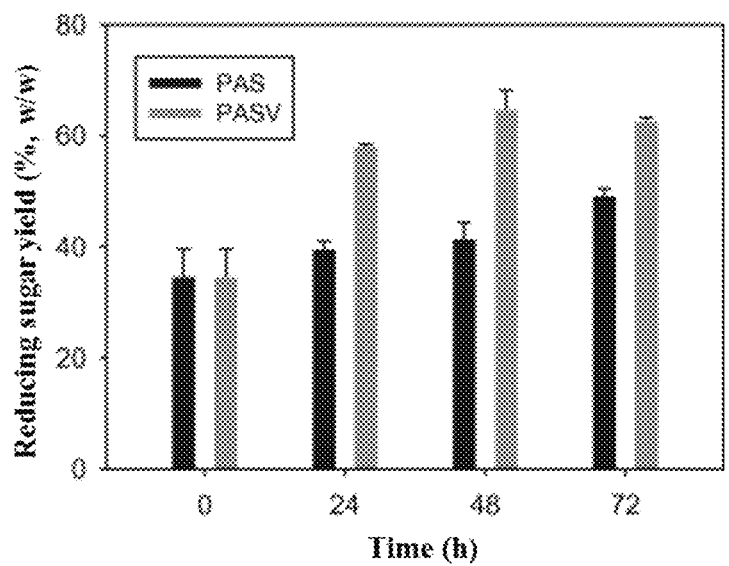

[FIG. 3]
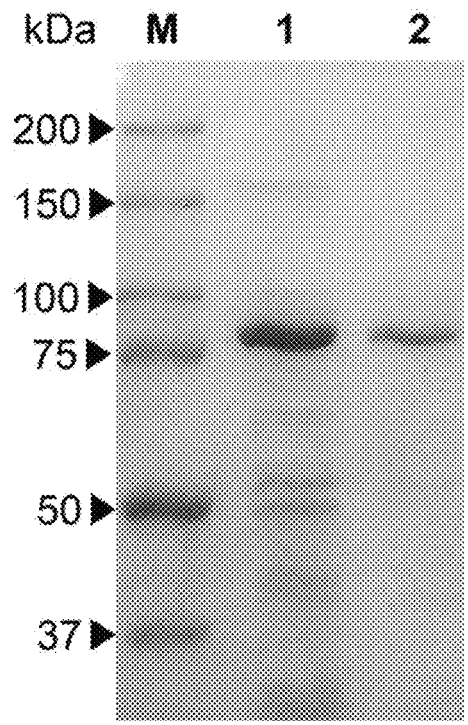
[FIG. 4A]
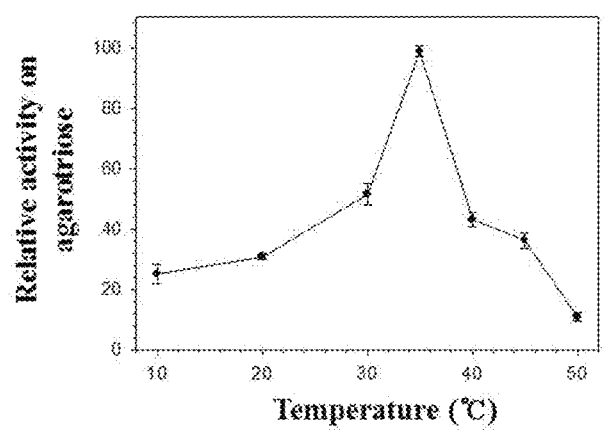

[FIG. 4B]
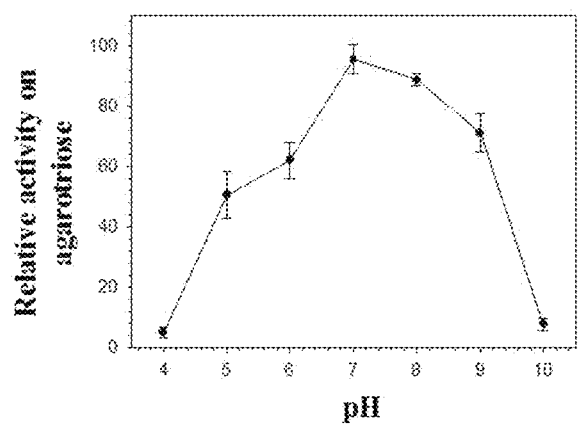
[FIG. 5A]
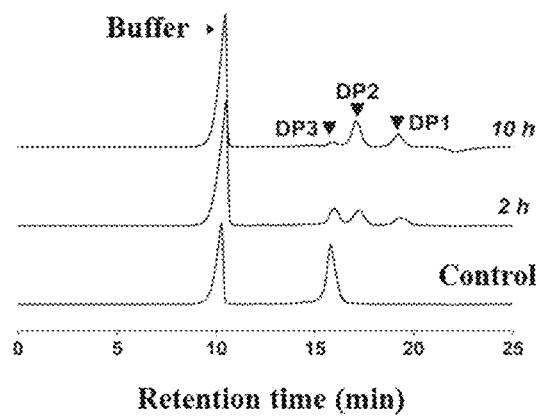
[FIG. 5B]
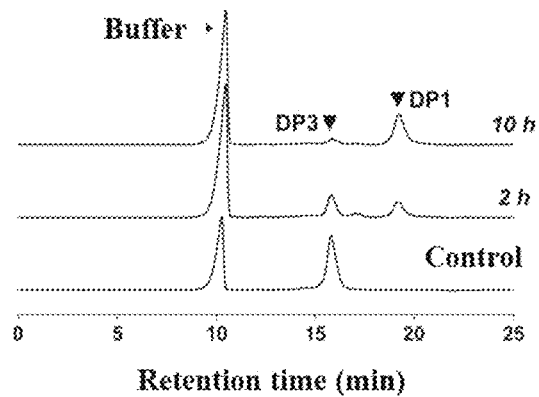

[FIG. 6A]
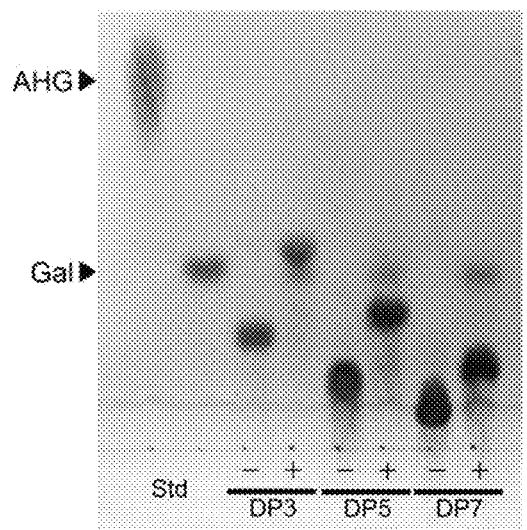
[FIG. 6B]
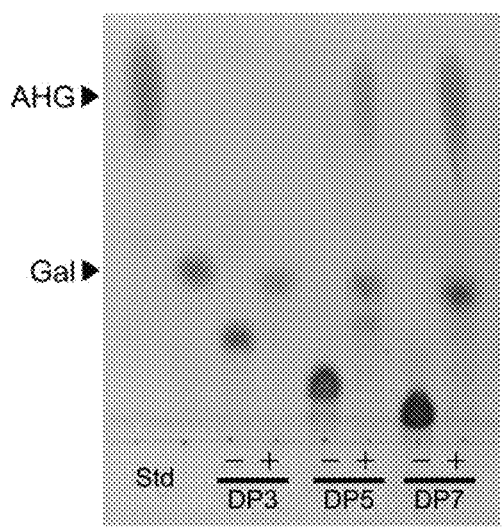

[FIG. 7]
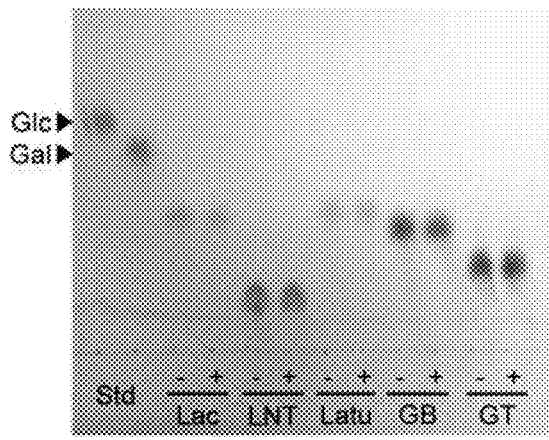
[FIG. 8A]
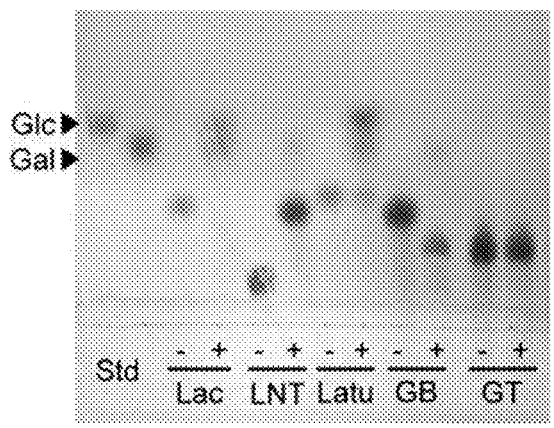
[FIG. 8B]
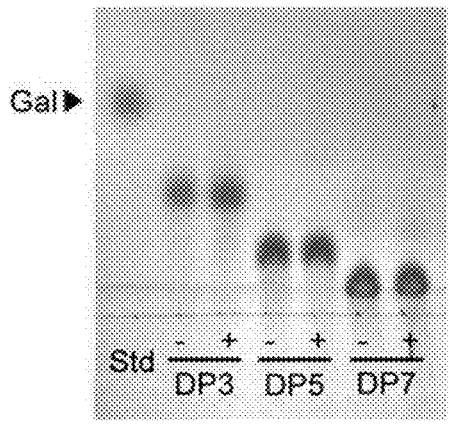

[FIG. 9]
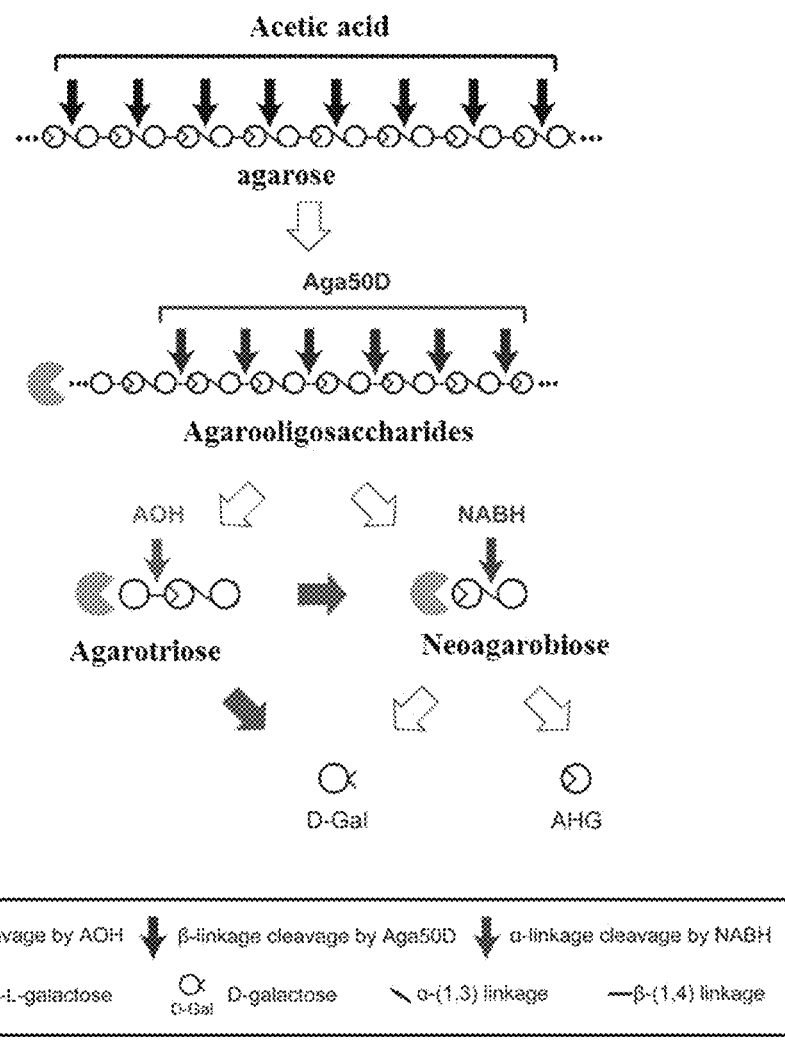

SEQUENCE LISTING

<160> NUMBER OF SEQ ID NOS: 4

<210> SEQ ID NO 1
<211> LENGTH: 806
<212> TYPE: PRT
<213> ORGANISM: Vibrio sp. EJY3

<400> SEQUENCE: 1

```
Met His Asn Ser Pro Arg Ser Thr Thr Leu Phe Asn Asp Asn Trp Leu
1               5                   10                  15

Phe Gln Leu Ala Lys Asp Lys Pro Asn Thr Lys Gln Trp Ser Thr Val
            20                  25                  30

Thr Leu Pro His Asp Trp Ser Val Ala Ser Ala Phe Ser Pro Gln Tyr
        35                  40                  45

Asp Gly Ala Thr Gly Tyr Leu Pro Gly Gly Ile Gly Trp Tyr Lys Lys
    50                  55                  60

Gln Phe Lys Asn Pro Leu Asn Lys His Tyr Ser Arg Cys Ile Leu Val
65                  70                  75                  80

Phe Asp Gly Ile Tyr Asn Asn Ala Thr Ile Asn Ile Asn Gly Tyr Asp
                85                  90                  95

Ile His Phe Gln Ala Tyr Gly Tyr Ala Pro Phe Asn Ile Glu Ile Thr
            100                 105                 110

Asp Tyr Leu Lys Ser Asp Asn Val Ile Thr Ile His Val Asp Arg Arg
        115                 120                 125

Arg Tyr Ile Asp Ser Arg Trp Tyr Thr Gly Ser Gly Ile Tyr Arg Asp
    130                 135                 140

Ile Glu Met Val Leu Thr Lys Asp Val Phe Val Pro Ile Trp Glu Asn
145                 150                 155                 160

His Ile Lys Ala Ser Val Ser Ser Asn Gln Ile Gly His Ile His Gln
                165                 170                 175

Gln Leu Met Ile Glu Ala Lys Thr Lys Thr His Tyr Leu Thr Ile Val
            180                 185                 190

Ser Arg Leu Leu Glu Pro Asn Ser Asp Asn Cys Val Ala Thr Ala Arg
        195                 200                 205

Thr His Arg Ser Val Asn Asn Arg Glu Val Cys Asp Leu Glu Leu Thr
    210                 215                 220

Cys Asp Gln Leu Ser Leu Trp Ser Pro Asp Ser Pro Ile Leu Tyr Lys
225                 230                 235                 240

Leu Glu Thr Gln Ile Tyr Glu Asn Gly Cys Val Ile Asp Lys Val Ser
                245                 250                 255

Glu Asn Ile Gly Phe Arg Ser Ile Glu Phe Ser Pro Glu Gln Gly Phe
            260                 265                 270

Phe Leu Asn Gly Met Pro Thr Lys Val Arg Gly Val Cys Leu His His
        275                 280                 285

Asp Gly Gly Leu Val Gly Ala Ala Val Pro Asp Glu Ile Trp Ile Arg
    290                 295                 300

Arg Leu Ser Lys Leu Lys Gln Cys Gly Val Asn Ala Ile Arg Ile Ala
305                 310                 315                 320

His Asn Pro Ala Ser Lys Arg Leu Leu His Leu Cys Asp Thr Met Gly
                325                 330                 335

Phe Leu Val Gln Asp Glu Phe Asp Glu Trp Asp Tyr Pro Lys Asp
            340                 345                 350

Lys Arg Leu Asn Met Gly Asn Gln His Asp Asp Phe Phe Ser Gln Cys
        355                 360                 365
```

```
Tyr Thr Glu His Phe Gln Thr Arg Ala Lys Thr Asp Leu Cys Asn Thr
370                 375                 380

Leu Lys Cys His Ile Asn His Pro Ser Ile Phe Met Trp Ser Ile Gly
385                 390                 395                 400

Asn Glu Ile Glu Trp Thr Tyr Pro Arg Asn Val Glu Ala Thr Gly Phe
            405                 410                 415

Phe Asp Ala Ser Trp Asp Gly Asn Tyr Phe Trp Ser Leu Pro Pro Asn
        420                 425                 430

Ser Pro Asp Glu Ile Lys Asp Lys Leu Lys Asn Leu Pro Gln His Thr
    435                 440                 445

Tyr Asp Ile Gly Lys Thr Ala Asn Lys Leu Ala Arg Trp Val Lys Ala
450                 455                 460

Ile Asp Gln Thr Arg Pro Ile Thr Ala Asn Cys Ile Leu Pro Ser Ser
465                 470                 475                 480

Ser Tyr His Ser Gly Tyr Ala Asp Ala Leu Asp Val Ile Gly Phe Ser
            485                 490                 495

Tyr Arg Val Val Tyr Asp Tyr Gly His Glu Ile Arg Pro Asn Leu
        500                 505                 510

Pro Ile Ile Gly Asn Glu Asn Leu Pro Gln Trp His Glu Trp Lys Ala
        515                 520                 525

Val Leu Glu Arg Asn His Val Ser Gly Leu Phe Leu Trp Thr Gly Ile
530                 535                 540

Asn Tyr Met Gly Glu Ser His Gly Lys Trp Pro Val Arg Thr Thr Asp
545                 550                 555                 560

Ser Gly Leu Leu Asp Thr Ala Gly Phe Glu Lys Pro Ser Tyr Ala Leu
            565                 570                 575

Phe Lys Ser Leu Trp Thr Asp Glu Pro Tyr Val Lys Val Phe Thr Gln
        580                 585                 590

Arg Ala Asp Leu Thr Gln Leu Lys Phe Asp Glu Gln Thr Phe Val Ala
    595                 600                 605

Phe Glu His Asp Glu Asn Ala Trp Gln Lys Lys Leu Trp Val Trp Asp
610                 615                 620

Glu Arg Asn Ser His Trp Asn Tyr Glu Asn Glu Gln Trp Val Thr Ile
625                 630                 635                 640

Glu Ala Tyr Ser Asn Cys Pro Gln Val Gln Leu Tyr Leu Asn Asp Glu
            645                 650                 655

Leu Val Gly Thr Gln Gln Leu Glu Lys Gln Ile Asp Arg Val Phe Arg
        660                 665                 670

Trp Ala Leu Pro Tyr Arg Ala Gly Lys Ile Ser Leu Val Gly Leu Lys
    675                 680                 685

Asn Asp Val Glu Val Thr Arg Asp Glu Ile Val Thr Ser Gly Val Pro
690                 695                 700

Arg Lys Ile Ser Ile Val Asp Glu Thr His Glu Gly Ser Ser Ser Tyr
705                 710                 715                 720

Arg Gln Leu Ile Val Gln Met Leu Asp Lys Asp Asn His Pro Val Ser
            725                 730                 735

His Glu Glu Ala Leu Leu Glu Phe Arg Val Arg Gly Cys Glu Trp Ile
        740                 745                 750

Gly Ala Asp Asn Gly Ser Ile Ser Ile Asn Ala Tyr Asn Ser Pro
    755                 760                 765

Thr Ile Ala Thr Arg His Gly Arg Val Leu Ala Val Val Lys Ser Ser
770                 775                 780

Gln Gly Gln Ser Gly Asp Ile Glu Ile Tyr Ser Asn Ser Gly Val Lys
```

```
                785                 790                 795                 800
Ala Ser Phe Ser Leu Leu
            805

<210> SEQ ID NO 2
<211> LENGTH: 2421
<212> TYPE: DNA
<213> ORGANISM: Vibrio sp. EJY3

<400> SEQUENCE: 2
atgcacaatt caccgagaag taccacatta tttaacgaca actggctttt tcagttggca       60
aaagataaac cgaataccaa acaatggtcg acggttacgc ttccccacga ttggagtgta      120
gcttcggcct tttctccaca gtatgatgga gccacgggtt acctacctgg gggaattggt      180
tggtacaaaa agcagtttaa aaatcctcta aataaacact attcgcgctg tatactcgtt      240
tttgacggga tttacaacaa tgcaaccatt aatatcaatg gctatgatat acatttccaa      300
gcgtatggtt atgcgccatt caatatagaa attactgatt acttgaaatc agacaatgta      360
attactatcc atgtcgatag acgcaggtat atcgacagta ggtggtatac aggttcaggt      420
atttaccgtg atatagaaat ggttctaact aaggatgtgt tgttcctat ttgggaaaat       480
catataaaag cttccgttag ctcaaaccag attggccata tccaccagca actgatgatt      540
gaagcaaaaa cgaaaacgca ttacttgaca attgtaagtc gtttgctcga gcccaattcc      600
gataattgcg tagctacagc tcgaacgcat cgttcagtga caatcgaga gtatgtgat       660
ttagaactaa cgtgtgatca actgagcctt tggagcccag attaccaat tctttataag       720
ttggaaactc aaatctacga aaatggctgc gtcattgata aggtatctga aacattggt       780
tttcgtagca tagagttttc gccagaacag gggttttcc tcaatgggat gccaactaaa       840
gtccgtgggg tctgccttca tcatgatggc ggactcgttg gcgctgccgt acctgatgaa      900
atatggatac gtcggttgtc aaagctcaaa caatgtggtg taaatgcaat aagaatcgca      960
cacaacccag cctccaagcg tctattgcac ctctgtgaca cgatgggatt tctggtgcag     1020
gatgagtttt ttgacgagtg ggattatcct aaagataaac gccttaacat gggcaaccaa     1080
cacgatgact ttttcagcca atgttacacc gagcactttc aaacccgagc aaaaaccgat     1140
ctttgtaata cgttgaaatg ccatattaac catccatcaa tattcatgtg gagtattggc     1200
aacgaaattg agtggaccta cccacgcaac gtcgaagcaa cgggcttttt tgatgcaagt     1260
tgggatggga attatttctg gagcttacca cctaactctc ccgatgaaat aaaagataaa     1320
ctcaaaaatt tgccacagca cacttatgat attggggaaaa ctgcgaacaa gcttgctcgt     1380
tgggtaaaag ctatcgatca aactcgaccg attactgcca actgtatcct tccatcatcc     1440
agctaccatt caggttacgc cgacgcgctc gatgtaattg gatttagtta cgacgtgtt      1500
gtatatgatt atgggcatga aatcagacct aacctgccga taatcggtaa tgaaaattta     1560
cctcaatggc atgaatggaa agcagtgctt gaacgcaacc atgtatccgg attgtttctt     1620
tggactggaa tcaattatat gggagaatct catggtaaat ggcctgtaag aaccactgac     1680
agcggcctgc tagacaccgc tgggtttgaa aaaccaagtt atgcgctttt taaatcgctg     1740
tggacagacg aaccttatgt caaagtattt actcaacgag cagacttaac acaactgaag     1800
tttgacgagc aaacttttgt tgcctttgaa catgatgaaa atgcttggca aaaaaaatta     1860
tgggtctggg acgaaagaaa ctcgcactgg aattatgaaa atgagcaatg ggtcactatc     1920
gaagcctata gcaactgtcc gcaggtacaa ctctacctca acgatgagtt ggttggaacc     1980
```

-continued

```
caacagttag aaaagcaaat cgacagagtc tttcgttggg ccttaccata tagagcagga    2040
aagatctctc tggttggttt aaagaacgac gtagaggtaa ctagagatga aattgtcacg    2100
tctggagtgc cgaggaagat ctcgattgta gatgaaaccc atgaaggttc aagctcatac    2160
cggcaactta tagtccagat gcttgataaa gacaaccatc cagtgagtca tgaagaagca    2220
ttgttagagt ttcgtgttcg cggttgtgaa tggattggag ccgataatgg cagtatatct    2280
tctatcaacg catataatag cccaacgatt gctacacgtc atggcagagt tttagcagtt    2340
gtaaaatcat cgcagggtca aagtggtgat atcgaaattt actcaaattc aggagtgaaa    2400
gcctcttttt cactacttta a                                              2421
```

<210> SEQ ID NO 3
<211> LENGTH: 747
<212> TYPE: PRT
<213> ORGANISM: Saccharophagus degradans 2-40

<400> SEQUENCE: 3

```
Met Leu Phe Asp Phe Glu Asn Asp Gln Val Pro Ser Asn Ile His Phe
1               5                   10                  15

Leu Asn Ala Arg Ala Ser Ile Glu Thr Tyr Thr Gly Ile Asn Gly Glu
            20                  25                  30

Pro Ser Lys Gly Leu Lys Leu Ala Met Gln Ser Lys Gln His Ser Tyr
        35                  40                  45

Thr Gly Leu Ala Ile Val Pro Glu Gln Pro Trp Asp Trp Ser Glu Phe
    50                  55                  60

Thr Ser Ala Ser Leu Tyr Phe Asp Ile Val Ser Val Gly Asp His Ser
65                  70                  75                  80

Thr Gln Phe Tyr Leu Asp Val Thr Asp Gln Asn Gly Ala Val Phe Thr
                85                  90                  95

Arg Ser Ile Asp Ile Pro Val Gly Lys Met Gln Ser Tyr Tyr Ala Lys
            100                 105                 110

Leu Ser Gly His Asp Leu Glu Val Pro Asp Ser Gly Asp Val Asn Asp
        115                 120                 125

Leu Asn Leu Ala Ser Gly Leu Arg Ser Asn Pro Pro Thr Trp Thr Ser
    130                 135                 140

Asp Asp Arg Gln Phe Val Trp Met Trp Gly Val Lys Asn Leu Asp Leu
145                 150                 155                 160

Ser Gly Ile Ala Lys Ile Ser Leu Ser Val Gln Ser Ala Met His Asp
                165                 170                 175

Lys Thr Val Ile Ile Asp Asn Ile Arg Ile Gln Pro Asn Pro Pro Gln
            180                 185                 190

Asp Glu Asn Phe Leu Val Gly Leu Val Asp Glu Phe Gly Gln Asn Ala
        195                 200                 205

Lys Val Asp Tyr Lys Gly Lys Ile His Ser Leu Glu Glu Leu His Ala
    210                 215                 220

Ala Arg Asp Val Glu Leu Ala Glu Leu Asp Gly Lys Pro Met Pro Ser
225                 230                 235                 240

Arg Ser Lys Phe Gly Gly Trp Leu Ala Gly Pro Lys Leu Lys Ala Thr
                245                 250                 255

Gly Tyr Phe Arg Thr Glu Lys Ile Asn Gly Lys Trp Met Leu Val Asp
            260                 265                 270

Pro Glu Gly Tyr Pro Tyr Phe Ala Thr Gly Leu Asp Ile Ile Arg Leu
        275                 280                 285

Ser Asn Ser Ser Thr Met Thr Gly Tyr Asp Tyr Asp Gln Ala Thr Val
```

```
              290                 295                 300
Ala Gln Arg Ser Ala Asp Asp Val Thr Pro Glu Asp Ser Lys Gly Leu
305                 310                 315                 320

Met Ala Val Ser Glu Lys Ser Phe Ala Thr Arg His Leu Ala Ser Pro
                325                 330                 335

Thr Arg Ala Ala Met Phe Asn Trp Leu Pro Asp Tyr Asp His Pro Leu
                340                 345                 350

Ala Asn His Tyr Asn Tyr Arg Arg Ser Ala His Ser Gly Pro Leu Lys
                355                 360                 365

Arg Gly Glu Ala Tyr Ser Phe Tyr Ser Ala Asn Leu Glu Arg Lys Tyr
370                 375                 380

Gly Glu Thr Tyr Pro Gly Ser Tyr Leu Asp Lys Trp Arg Glu Val Thr
385                 390                 395                 400

Val Asp Arg Met Leu Asn Trp Gly Phe Thr Ser Leu Gly Asn Trp Thr
                405                 410                 415

Asp Pro Ala Tyr Tyr Asp Asn Asn Arg Ile Pro Phe Phe Ala Asn Gly
                420                 425                 430

Trp Val Ile Gly Asp Phe Lys Thr Val Ser Ser Gly Ala Asp Phe Trp
                435                 440                 445

Gly Ala Met Pro Asp Val Phe Asp Pro Glu Phe Lys Val Arg Ala Met
450                 455                 460

Glu Thr Ala Arg Val Val Ser Glu Glu Ile Lys Asn Ser Pro Trp Cys
465                 470                 475                 480

Val Gly Val Phe Ile Asp Asn Glu Lys Ser Phe Gly Arg Pro Asp Ser
                485                 490                 495

Asp Lys Ala Gln Tyr Gly Ile Pro Ile His Thr Leu Gly Arg Pro Ser
                500                 505                 510

Glu Gly Val Pro Thr Arg Gln Ala Phe Ser Lys Leu Leu Lys Ala Lys
                515                 520                 525

Tyr Lys Thr Ile Ala Ala Leu Asn Asn Ala Trp Gly Leu Lys Leu Ser
                530                 535                 540

Ser Trp Ala Glu Phe Asp Leu Gly Val Asp Val Lys Ala Leu Pro Val
545                 550                 555                 560

Thr Asp Thr Leu Arg Ala Asp Tyr Ser Met Leu Leu Ser Ala Tyr Ala
                565                 570                 575

Asp Gln Tyr Phe Lys Val Val His Gly Ala Val Glu His Tyr Met Pro
                580                 585                 590

Asn His Leu Tyr Leu Gly Ala Arg Phe Pro Asp Trp Gly Met Pro Met
                595                 600                 605

Glu Val Val Lys Ala Ala Lys Tyr Ala Asp Val Val Ser Tyr Asn
610                 615                 620

Ser Tyr Lys Glu Gly Leu Pro Lys Gln Lys Trp Ala Phe Leu Ala Glu
625                 630                 635                 640

Leu Asp Lys Pro Ser Ile Ile Gly Glu Phe His Ile Gly Ala Met Asp
                645                 650                 655

His Gly Ser Tyr His Pro Gly Leu Ile His Ala Ala Ser Gln Ala Asp
                660                 665                 670

Arg Gly Glu Met Tyr Lys Asp Tyr Met Gln Ser Val Ile Asp Asn Pro
                675                 680                 685

Tyr Phe Val Gly Ala His Trp Phe Gln Tyr Met Asp Ser Pro Leu Thr
                690                 695                 700

Gly Arg Ala Tyr Asp Gly Glu Asn Tyr Asn Val Gly Phe Val Asp Val
705                 710                 715                 720
```

-continued

Thr Asp Thr Pro Tyr Gln Glu Met Val Asp Ala Ala Lys Glu Val Asn
                725                 730                 735

Ala Lys Ile Tyr Thr Glu Arg Leu Gly Ser Lys
            740                 745

<210> SEQ ID NO 4
<211> LENGTH: 368
<212> TYPE: PRT
<213> ORGANISM: Saccharophagus degradans 2-40

<400> SEQUENCE: 4

Met Ser Asp Ser Lys Val Asn Lys Lys Leu Ser Lys Ala Ser Leu Arg
1               5                   10                  15

Ala Ile Glu Arg Gly Tyr Asp Glu Lys Gly Pro Glu Trp Leu Phe Glu
            20                  25                  30

Phe Asp Ile Thr Pro Leu Lys Gly Asp Leu Ala Tyr Glu Glu Gly Val
        35                  40                  45

Ile Arg Arg Asp Pro Ser Ala Val Leu Lys Val Asp Asp Glu Tyr His
    50                  55                  60

Val Trp Tyr Thr Lys Gly Glu Gly Glu Thr Val Gly Phe Gly Ser Asp
65                  70                  75                  80

Asn Pro Glu Asp Lys Val Phe Pro Trp Asp Lys Thr Glu Val Trp His
                85                  90                  95

Ala Thr Ser Lys Asp Lys Ile Thr Trp Lys Glu Ile Gly Pro Ala Ile
            100                 105                 110

Gln Arg Gly Ala Ala Gly Ala Tyr Asp Asp Arg Ala Val Phe Thr Pro
        115                 120                 125

Glu Val Leu Arg His Asn Gly Thr Tyr Tyr Leu Val Tyr Gln Thr Val
    130                 135                 140

Lys Ala Pro Tyr Leu Asn Arg Ser Leu Glu His Ile Ala Ile Ala Tyr
145                 150                 155                 160

Ser Asp Ser Pro Phe Gly Pro Trp Thr Lys Ser Asp Ala Pro Ile Leu
                165                 170                 175

Ser Pro Glu Asn Asp Gly Val Trp Asp Thr Asp Glu Asp Asn Arg Phe
            180                 185                 190

Leu Val Lys Glu Lys Gly Ser Phe Asp Ser His Lys Val His Asp Pro
        195                 200                 205

Cys Leu Met Phe Phe Asn Asn Arg Phe Tyr Leu Tyr Tyr Lys Gly Glu
    210                 215                 220

Thr Met Gly Glu Ser Met Asn Met Gly Gly Arg Glu Ile Lys His Gly
225                 230                 235                 240

Val Ala Ile Ala Asp Ser Pro Leu Gly Pro Tyr Thr Lys Ser Glu Tyr
                245                 250                 255

Asn Pro Ile Thr Asn Ser Gly His Glu Val Ala Val Trp Pro Tyr Lys
            260                 265                 270

Gly Gly Met Ala Thr Met Leu Thr Thr Asp Gly Pro Glu Lys Asn Thr
        275                 280                 285

Cys Gln Trp Ala Glu Asp Gly Ile Asn Phe Asp Ile Met Ser His Ile
    290                 295                 300

Lys Gly Ala Pro Glu Ala Val Gly Phe Phe Arg Pro Glu Ser Asp Ser
305                 310                 315                 320

```
Asp Asp Pro Ile Ser Gly Ile Glu Trp Gly Leu Ser His Lys Tyr Asp
            325                 330                 335

Ala Ser Trp Asn Trp Asn Tyr Leu Cys Phe Phe Lys Thr Arg Arg Gln
            340                 345                 350

Val Leu Asp Ala Gly Ser Tyr Gln Gln Thr Gly Asp Ser Gly Ala Val
            355                 360                 365
```

AGAROOLIGOSACCHARIDE HYDROLASE AND METHOD FOR PRODUCING 3,6-ANHYDRO-L-GALACTOSE AND GALACTOSE FROM AGAROSE BY USING SAME

CROSS-REFERENCE TO RELATED APPLICATIONS

This application is a U.S. National Phase of International Patent Application No.: PCT/KR2014/009470, filed Oct. 8, 2014, which claims priority to Korea Patent Application No. 10-2013-0121990, filed Oct. 14, 2013, the disclosures of which are incorporated herein by reference.

TECHNICAL FIELD

The present invention relates to a novel β-agarooligosaccharide hydrolase having hydrolytic activity for agarooligosaccharides and to a method of producing 3,6-anhydro-L-galactose and galactose from agarose by using the same.

BACKGROUND ART

Compared to plant biomass currently used in many areas, algae have a lower content of recalcitrant components, such as lignin to use. Therefore, algae are advantageous in that they can be converted much more easily into a monosaccharide which is a substrate for producing bioenergy and biochemicals. Also, by not using food resources, algae are free from the problem of using food resources in producing energy. For these reasons, algae are receiving attention as important biomass in an aspect of the production of biochemicals including alternative energy.

Among algae, especially red algae (e.g., *Gelidium amansii*) is not only a raw material for the production of such bioenergy and biochemicals, but is also reported to contain agarooligosaccharides, which exhibit excellent physiological activity such as antioxidation, anti-inflammation, anti-cancer, anti-allergy, whitening, and moisturization, as a component, such that it is usefully employed in pharmaceutical and cosmetic fields (U.S. Pat. No. 7,662,2291 by Tomono et al. (2009); U.S. Patent No. 69/143,282 by Enoki et al. (2005)).

As a main constituent, red algae contain agarose which is a polymer having neoagarobiose (i.e. 3,6-anhydro-L-galactose and D-galactose bonded by an α-1,3-linkage) as a basic unit that is connected with another unit by a β-1,4-linkage. The present inventors empirically proved the fact that the physiological functionality of 3,6-anhydro-L-galactose (Yun et at (2013) *Appl Microbiol Biotechnol.* 97(7):2961-70). Also reported in relation to the production of the 3,6-anhydro-L-galactose is a preparation process of 3,6-anhydro-L-galactose and D-galactose by a mild chemical pretreatment and enzymatic saccharification to replace chemical treatment methods (Jol et at (1999) *Anal Biochem.* 268, 213-222; Kim et at (2010) *Bull Korean Soc.* 31(2) 511-514) that have problems of a very low yield and a high possibility of excessive hydrolysis.

Agarose is depolymerized by an exo-type Aga50D enzyme after a chemical pretreatment into neoagarobiose and agarotriose (D-galactose-β-1,4 linkage-3,6-anhydro-L-galactose-α-1,3 linkage-D-galactose) which are main reaction products. Then, the neoagarobiose is ultimately hydrolyzed into 3,6-anhydro-L-galactose and D-galactose by SdNABH (Korean Patent No. 10-1293668), which is an α-neoagarobiose hydrolase. During this process, a chemical pretreatment under mild conditions is essential to improve the reactivity of the Aga50D enzyme. However, agarotriose produced using a chemically pretreated substrate cannot be ultimately decomposed into 3,6-anhydro-L-galactose and D-galactose and remains as a reaction residue.

If the remaining agarotriose could be ultimately decomposed into 3,6-anhydro-L-galactose and D-galactose, a larger improvement in the production yield of 3,6-anhydro-L-galactose and D-galactose would be expected. Since endo-type and exo-type β-agarases cannot hydrolyze a substrate such as agarotriose, another approach of decomposing agarotriose into D-galactose and neoagarobiose using a β-galactosidase was tried, but commercially available β-galactosidases did not show hydrolytic activity for agarooligosaccharides.

DISCLOSURE

Technical Problem

The present invention is directed to providing a method of improving efficiency of agarose saccharification using a novel enzyme having hydrolytic activity for agarooligosaccharides.

The present invention is also directed to providing a method of producing galactose using a novel enzyme having hydrolytic activity for agarooligosaccharides.

Technical Solution

To achieve the above objectives, the present invention provides a composition for agarose saccharification comprising an agarase; a β-agarooligosaccharide hydrolase having hydrolytic activity for agarotriose and represented by an amino acid sequence of SEQ ID NO:1; and an α-neoagarobiose hydrolase.

The present invention also provides a method of saccharifying agarose by reacting a substrate and a composition for agarose saccharification according to the present invention, wherein the substrate is selected from the group consisting of agarose, agarotriose, and neoagarobiose.

The present invention also provides a composition for producing galactose comprising a β-agarooligosaccharide hydrolase having hydrolytic activity for agarotriose, agaropentaose, or agaroheptaose and represented by an amino acid sequence of SEQ ID NO:1.

In addition, the present invention provides a method of producing galactose by reacting a substrate and the β-agarooligosaccharide hydrolase of the present invention, wherein the substrate is selected from the group consisting of agarotriose, agaropentaose and agaroheptaose.

Advantageous Effects

The present invention is effective in improving the production yield of 3,6-anhydro-L-galactose and D-galactose from agarose, in other words, saccharification yield, by utilizing a β-agarooligosaccharide hydrolase showing activity toward agarotriose hydrolysis to galactose and neoagarobiose.

DESCRIPTION OF DRAWINGS

FIG. 1 is a TLC image of reaction products for various enzymes (PA: pretreated agarose, PAS: reaction products of Aga50D and SdNABH, with respect to the pretreated agarose, PASV: reaction products of Aga50D, SdNABH, and additionally a *Vibrio* sp. EJY3 crude enzyme with respect to the pretreated agarose).

FIG. 2 shows reducing equivalents of PAS and PASV of FIG. 1 measured by a DNS assay and summarized in a bar graph.

FIG. 3 is an SDS-PAGE image of a purified β-agarooligosaccharide hydrolase of the present invention.

FIGS. 4A and 4B show optimal temperature and pH results of the β-agarooligosaccharide hydrolase of the present invention. FIG. 4A shows the optimal pH of the β-agarooligosaccharide hydrolase with respect to an agarotriose substrate, and FIG. 4B shows the optimal temperature of the β-agarooligosaccharide hydrolase with respect to the agarotriose substrate (M: protein marker; Lane 1: the β-agarooligosaccharide hydrolase purified primarily using a HisTrap HP column; Lane 2: the β-agarooligosaccharide hydrolase purified secondarily using a HisTrap Q FF column).

FIGS. 5A and 5B illustrate the enzymatic activity of β-agarooligosaccharide hydrolase of the present invention on an agarotriose substrate. FIG. 5A is an HPLC result showing changes in the substrate and products in various reaction time between the β-agarooligosaccharide hydrolase and the agarotriose substrate, and FIG. 5B is an HPLC result showing changes in the substrate and products in various reaction time between the β-agarooligosaccharide hydrolase plus α-neoagarobiose hydrolase and the agarotriose substrate.

FIGS. 6A and 6B show the enzymatic activity of β-agarooligosaccharide hydrolase of the present invention on agarotriose, agaropentaose, and agaroheptaose substrates. FIG. 6A shows the reaction products of the β-agarooligosaccharide hydrolase on each substrate by TLC and FIG. 6B shows the reaction products of the β-agarooligosaccharide hydrolase and α-neoagarobiose hydrolase on each substrate by TLC.

FIG. 7 shows the enzymatic activity of β-agarooligosaccharide hydrolase of the present invention on various substrates (as standards, glucose, and galactose standards were used).

FIGS. 8A and 8B show the enzymatic activity of *E. coli*-derived β-galactosidase on various substrates (as standards, glucose, and galactose standards were used). FIG. 8A shows the results of an enzyme reaction on each of lactose, lacto-N-neotetraose, lactulose, 4-β-galactobiose, and α-1,3-β-1,4-galactotriose, and FIG. 8B shows the results of an enzyme reaction on each of agarotriose, agaropentaose, and agaroheptaose.

FIG. 9 is a schematic diagram for showing an agarose saccharification process using the β-agarooligosaccharide hydrolase (β-AOH) of the present invention.

BEST MODE

Hereinafter, the components of the present invention will be described in detail.

The present invention relates to a composition for agarose saccharification comprising an agarase; a β-agarooligosaccharide hydrolase having hydrolytic activity for agarotriose and represented by an amino acid sequence of SEQ ID NO:1; and a neoagarobiose hydrolase.

The composition for agarose saccharification of the present invention is characterized in that agarotriose, which used to remain unhydrolyzed in the conventional art, is effectively hydrolyzed such that the production efficiency of 3,6-anhydro-L-galactose and D-galactose from agarose (i.e. an efficiency of agarose saccharification) is significantly improved by utilizing a β-agarooligosaccharide hydrolase which hydrolyzes agarotriose that is a product of agarooligosaccharide hydrolysis into neoagarobiose and D-galactose for agarose saccharification.

According to one embodiment of the present invention, checked results of reducing equivalents from a DNS method show that the rate of saccharification is about 20% when an agarose is only pretreated, and that the rate increases up to 50% when a conventional enzymatic treatment (i.e. a treatment with agarase and neoagarobiose hydrolase) is employed. In contrast, when β-agarooligosaccharide hydrolase is additionally treated to hydrolyze agarotriose during the enzymatic treatment, the rate of saccharification is 70%.

The β-agarooligosaccharide hydrolase does not exhibit activity that a β-galactosidase reportedly shows. Instead, by acting on a non-reducing end of not just agarotriose but also of various agarooligosaccharides (n) such as agaropentaose and agaroheptaose, the β-agarooligosaccharide hydrolase can hydrolyze agarooligosaccharide into D-galactose and neoagarobiose (n−1).

The β-agarooligosaccharide hydrolase may originate from *Vibrio* sp. EJY3 but is not limited thereto.

The β-agarooligosaccharide hydrolase encompasses not only the amino acid sequence represented by SEQ ID NO: 1 but also a protein as a mutated protein of the enzyme with one or more of substitution, deletion, transposition, addition, etc. that has the hydrolytic activity for agarotriose in the scope of the enzyme of the present invention and, preferably, includes an amino acid sequence having a sequence identity of 80% or more, 85% or more, 90% or more, 93% or more, 94% or more, 95% or more, 96% or more, 97% or more, 98% or more, and 99% or more with the amino acid sequence disclosed in SEQ ID NO: 1 (also referred to as 'AOH').

In the present invention, a polypeptide having a certain percentage (e.g. 80%, 85%, 90%, 95%, or 99%) of sequence identity with respect to another sequence signifies that, when aligning the two sequences and comparing them, their amino acid residues are mutually the same by the above ratio. The alignment and percentage homology (or identity) may be determined using any suitable software program known in the art, such as those disclosed in the literature [CURRENT PROTOCOLS IN MOLECULAR BIOLOGY (F. M. Ausubel et al. (eds) 1987 Supplement 30 section 7.7.18)]. Preferred programs include GCG Pileup program, FASTA (Pearson et al. 1988 *Proc. Natl Acad. Sci USA* 85:2444-2448), and BLAST (BLAST Manual, Altschul et al., Natl. Cent. Biotechnol. Inf., Natl Lib. Med. (NCIB NLM NIH), Bethesda, Md., and Altschul et al. 1997 NAR25:3389-3402). Another preferred alignment program is ALIGN Plus (Scientific and Educational Software, PA), which preferably uses default parameters. Another available sequence software program is TFASTA Data Searching Program that is usable in Sequence Software Package Version 6.0 (Genetics Computer Group, University of Wisconsin, Madison, Wis.).

In the present specification, "protein" and "polypeptide" are used interchangeably herein. A conventional one-letter or three-letter code is used herein for amino acid residues.

In the present invention, when used with respect to cells, nucleic acids, proteins, or vectors, the term "recombinant" signifies that the cells, the nucleic acids, the proteins, or the vectors were modified by the introduction of heterologous nucleic acids or proteins, or the modification by alteration of the natural nucleic acid or proteins, or, alternatively, the term may refer to cells that originated from the modified cells. In other words, for example, a recombinant cell expresses a gene that is not seen in the inherent (non-recombinant) form of the cell, or, alternatively, it expresses an original gene that is expressed abnormally or is not expressed at all.

In the present specification "nucleic acid" encompasses a single-strand or double-strand DNA, RNA, and chemical variants thereof "Nucleic acid" and "polynucleotide" may be used interchangeably herein. Since the genetic code is degenerate, one or more codons may be used to encode a particular amino acid, and the present invention encompasses a polynucleotide encoding a particular amino acid sequence.

The term "introduction" used for inserting a nucleic acid sequence into a cell refers to "transfection," "transformation," or "transduction," and includes a reference to an integration into eukaryotic or prokaryotic cells of the nucleic acid sequence. In this case, the nucleic acid sequence is integrated into the genome (e.g. chromosome, plasmid, plastid, or mitochondrial DNA) of the cell to be converted to an autonomous replicon or transiently expressed.

The β-agarooligosaccharide hydrolase may be transcribed or translated not just in a region in upstream or downstream of a coding region of an enzyme but also by a DNA segment, that is, a coding gene, associated with the production of a polypeptide and including intervening sequences between individual coding segments. For example, the transcription or translation may be achieved by the sequence of SEQ ID NO: 2 but not limited thereto.

The β-agarooligosaccharide hydrolase may be isolated from a supernatant of a *Vibrio* sp. EJY3 culture and purified, and, by utilizing recombinant genetic engineering techniques, the β-agarooligosaccharide hydrolase can be produced and isolated by stains other than *Vibrio* sp. EJY3, artificial chemical synthesis methods, or the like.

When using recombinant techniques, factors used for ease of expression of common recombinant proteins, such as genes resistant to antibiotics, and reporter proteins or peptides that can be used for affinity column chromatography may be used, and such techniques are in a scope in which it can be easily conducted by a person of ordinary skill in the technical field to which the present invention belongs. In addition, for example, a culture supernatant of a transformed *E. coli* may be used, instead of the β-agarooligosaccharide hydrolase of the present invention.

The β-agarooligosaccharide hydrolase may be purified using a HisTrap HP column and a HisTrap FF column. According to one embodiment, the molecular weight of the purified β-agarooligosaccharide hydrolase may be about 90 kDa, according to the results of SDS-PAGE analysis.

The β-agarooligosaccharide hydrolase is an enzyme that belongs to GH family 2, and when compared for activity with other β-galactosidases in the GH family 2, the reported conventional β-galactosidase does not exhibit the enzymatic activity of hydrolyzing agarotriose into D-galactose and neoagarobiose. However, only the β-agarooligosaccharide hydrolase of the present invention, which originates from *Vibrio* sp. EJY3, may show agarotriose hydrolysis activity.

The β-agarooligosaccharide hydrolase may exhibit optimal hydrolytic activity on agarotriose in a temperature range of about 30 to 40° C. and a pH range of about 5 to 9.6.

In addition, the composition for agarose saccharification of the present invention includes an agarase that hydrolyzes agarooligosaccharide to agarotriose and neoagarobiose, which is a disaccharide.

As the agarase, an enzyme (referred to as 'Aga50D') that breaks the β-1,4-glycosidic linkage between D-galactose and 3,6-anhydro-L-galactose of agarose may be used.

The agarase encompasses not only the amino acid sequence represented by SEQ ID NO: 3 but also a protein as a mutant protein of the enzyme with one or more of substitution, deletion, transposition, addition, etc. that has the agarooligosaccharide hydrolytic activity in the scope of the enzyme of the present invention and, preferably, includes an amino acid sequence having a sequence identity of 80% or more, 85% or more, 90% or more, 93% or more, 94% or more, 95% or more, 96% or more, 97% or more, 98% or more, and 99% or more with the amino acid sequence represented by SEQ ID NO: 3.

The enzyme may have originated from *Saccharophagus degradans* 2-40$^T$ but is not limited thereto.

The agarase may be isolated from a culture supernatant of *Saccharophagus degradans* 2-40$^T$ and purified, and, by utilizing recombinant genetic engineering techniques, the agarase can be produced and isolated by strains other than *Saccharophagus degradans*, artificial chemical synthesis methods, or the like.

When using recombinant techniques, a culture supernatant of an edible strain, for example, transformed yeast may be used, instead of the agarase.

In addition, the composition for agarose saccharification of the present invention includes α-neoagarobiose hydrolase (referred to as 'sdNABH') that may hydrolyze neoagarobiose into 3,6-anhydro-L-galactose and D-galactose.

The α-neoagarobiose hydrolase encompasses not only the amino acid sequence represented by SEQ ID NO: 4 but also a protein as a mutant protein of the enzyme with one or more of substitution, deletion, transposition, addition, etc. that exhibits the neoagarobiose hydrolytic activity in the scope of the enzyme of the present invention and, preferably, includes an amino acid sequence having a sequence identify 80% or more, 85% or more, 90% or more, 93% or more, 94% or more, 95% or more, 96% or more, 97% or more, 98% or more, and 99% or more with the amino acid sequence represented by SEQ ID NO: 4.

The enzyme may have originated from *Saccharophagus degradans* 2-40$^T$ but is not limited thereto.

The α-neoagarobiose hydrolase may be isolated from a culture supernatant of *Saccharophagus degradans* 2-40$^T$ and purified, and, by utilizing recombinant genetic engineering techniques, the α-neoagarobiose hydrolase can be produced and isolated by strains other than *Saccharophagus degradans* 2-40$^T$, artificial chemical synthesis methods, or the like.

When using recombinant techniques, a culture supernatant of an edible strain, for example, transformed yeast may be replaced for use.

The composition for agarose saccharification of the present invention may produce 3,6-anhydro-L-galactose and D-galactose from agarose either by reacting pretreated agarose with an enzyme mixture of the agarase, the β-agarooligosaccharide hydrolase, and the α-neoagarobiose hydrolase, or by allowing the agarase, the β-agarooligosaccharide hydrolase, and the α-neoagarobiose hydrolase to react sequentially with the pretreated agarose.

The present invention also relates to a method of saccharifying agarose by reacting a substrate and the composition for agarose saccharification according to the present invention, wherein the substrate is selected from the group consisting of agarose, agarotriose, and neoagarobiose.

The method of saccharifying agarose of the present invention is characterized in that an agarase (which is an exo-type β-agarase), a β-agarooligosaccharide hydrolase, and an α-neoagarobiose hydrolase are allowed to react with a pretreated agarose to produce 3,6-anhydro-L-galactose and D-galactose.

The pretreated agarose refers to an agarose that is treated with a weak acid to produce agarooligosaccharides.

The weak acid may be one or two or more of acetic acid, formic acid, succinic acid, citric acid, malic acid, maleic acid, oxalic acid, and the like.

Considering production cost and separation of salt after neutralization by the weak acid, it is preferred that the weak acid is used at a concentration in a range of 0.5 to 60% (w/v). More specifically, it may be used at a concentration in a range of 20 to 40% (w/v).

The reaction between the agarose and the weak acid may be carried out in a temperature range of 40 to 150° C. and under conditions of 100 to 200 rpm for a duration ranging from 30 minutes to 6 hours. When the ranges are satisfied, it may be possible to minimize the products of excessive hydrolysis of agarose using the weak acid.

The resulted reaction products are agarooligosaccharides and may be obtained in a powder form by washing and drying to remove the remaining weak acid and the products of excessive hydrolysis.

The wash solvent may be a low-grade alcohol having 1 to 6 carbons but not particularly limited thereto.

For the enzymatic hydrolysis of the obtained agarooligosaccharides, an exo-type agarase, a β-agarooligosaccharide hydrolase, and an α-neoagarobiose hydrolase are used.

The agarase hydrolyzes agarooligosaccharides into agarotriose and neoagarobiose, the β-agarooligosaccharide hydrolase hydrolyzes agarotriose into D-galactose and neoagarobiose, and the α-neoagarobiose hydrolase hydrolyzes neoagarobiose into D-galactose and 3,6-anhydro-L-galactose.

Therefore, the agarotriose that used to remain during the conventional enzymatic hydrolysis of agarooligosaccharides is hydrolyzed by the β-agarooligosaccharide hydrolase, resulting in an improvement in the production yield of D-galactose and 3,6-anhydro-L-galactose.

3,6-Anhydro-L-galactose and D-galactose may be produced by reacting the pretreated agarose with an enzyme mixture of an agarase, a β-agarooligosaccharide hydrolase, and an α-neoagarobiose hydrolase or by allowing the agarase, the β-agarooligosaccharide hydrolase, and the α-neoagarobiose hydrolase to react sequentially with the pretreated agarose.

The reaction between agarooligosaccharides and the enzyme mixture or the sequential reaction between agarooligosaccharides and the enzymes may be carried out in a temperature range of 20 to 40° C. and under conditions ranging from 0 to 200 rpm for a duration ranging from 30 minutes to 7 days. More specifically, they may be carried out in a temperature range of 25 to 35° C. and under conditions ranging from 100 to 150 rpm for a duration ranging from 1 to 4 days.

When the agarooligosaccharides are in a powder form, it may be dissolved in a conventional buffer solution for use but not limited thereto.

The present invention also relates to a composition for the production of galactose comprising a β-agarooligosaccharide hydrolase having hydrolytic activity for agarotriose, agaropentaose or agaroheptaose and represented by the amino acid sequence of SEQ ID NO:1

Also, the present invention provides a method of producing galactose by reacting a substrate and the β-agarooligosaccharide hydrolase of the present invention, wherein the substrate is selected from the group consisting of agarotriose, agaropentaose, and agaroheptaose.

The β-agarooligosaccharide hydrolase may originate from Vibrio sp. EJY3 but is not limited thereto.

Since the β-agarooligosaccharide hydrolase produces D-galactose and neoagarobiose from agarotriose, agaropentaose, or agaroheptaose, it can be used for producing D-galactose.

The enzyme reactions may be carried out in a temperature range of 20 to 40° C. and a pH range of 5 to 9.6.

Hereinafter, the present invention will be described in detail with reference to exemplary embodiments. However, the following exemplary embodiments are intended merely to exemplify the present invention, and the scope of the present invention is not limited thereto.

MODES OF THE INVENTION

<Example 1> Determination of Enzymatic Activity of β-Agarooligosaccharide Hydrolase from the Crude Enzyme Extract of Vibrio sp. EJY3

To confirm that Vibrio sp. EJY3 has enzymatic activity towards the hydrolysis of agarotriose, a crude extract was obtained and assessed for the activity.

To obtain the crude extract, Vibrio sp. EJY3 was grown up to the mid-exponential phase in a medium including sea salt, then 40 mL of culture medium was centrifuged, cells were disrupted using a sonicator, and the crude extract was obtained. Using agarose as the substrate, the hydrolysis products by β agarase were observed by TLC (composition of a TLC solvent: n-butanol:ethanol:water=3:1:1 by volume).

The TLC results of reaction products for various enzymes were shown in FIG. 1 based on 3,6-anhydro-L-galactose, galactose, neoagarobiose standards. PA represents agarose pretreated by a reaction with 3% acetic acid at 130° C. for 30 minutes, PAS is a product from a reaction between the pretreated agarose with an exo-type β agarase (Aga50D) plus an α-neoagarobiose hydrolase (SdNABH), and PASV is a product obtained when Vibrio sp. EJY3 cruse extract crude extract (or crude enzyme) is added to the PAS.

As seen in FIG. 1, a decrease in agarotriose was observed when Vibrio sp. EJY3 crude enzyme was additionally engaged in the reaction. From this, it could be confirmed that the Vibrio sp. EJY3 crude enzyme contained an enzyme that hydrolyzes agarotriose.

In addition, agarotriose was completely hydrolyzed, and reducing equivalents were measured by a reducing sugar quantification method (a DNS method—50 µl of a DNS reagent is mixed with 100 µl of an enzyme reaction product that is diluted 25 times, treated at 95° C. for 5 minutes, and then absorbance is measured at 540 nm).

As shown in FIG. 2, an increase in the production yield of 3,6-anhydro-L-galactose and galactose was confirmed. The rate of saccharification when only a pretreatment was performed was about 20%, but the rate increased up to 50% when an enzymatic pretreatment was performed. To this, an additional treatment with Vibrio sp. EJY3 crude enzyme resulted in a rate of saccharification of 70% which was thought to be attributed to an ultimate the agarotriose hydrolysis.

<Example 2> Investigation into 3-Agarooligosaccharide Hydrolase from the Enzyme Candidates of Vibrio sp. EJY3

Among the enzymes that were reported in relation to Vibrio sp. EJY3, 8 enzymes that reportedly had activity for an agarase and a β-galactosidase were cloned to produce a recombinant strain, and then each crude enzyme activity for agarotriose was assessed. Among these, only one enzyme (VEJY3_09170) was found to have hydrolytic activity for agarotriose. As confirmed through UniProt (http://www.uniprot.org) and based on full genome sequence data of *Vibrio* sp. EJY3 that the present inventors revealed for the first time, VEJY3_09170 was identified as an enzyme that was classified as a β-galactosidase based on its genetic sequence and belonged to GH family 2 with many other β-galactosidases. Then, *E. coli* rosetta (DE3) was used as a host for the recombinant strain, and pET-21a was used as a vector. A colony that was inoculated on a solid medium having an ampicillin concentration of 50 μg/mL and obtained by transformation was again inoculated into an LB (Luria broth) containing 50 μg/mL ampicillin and then incubated for 12 hours under the conditions of 37° C. and 220 rpm (two 20 mL volumes). Then, it was inoculated into two 3 L Erlenmeyer flasks, each containing 1 L of LB broth, and shaking cultured under the same conditions for 3 hours (OD=0.8), cooled in ice for 1 hour, and added 0.1 mM IPTG to induce an expression under conditions of 16° C. and 120 rpm for 12 hours. The culture medium was centrifuged (6000 rpm, 4° C., 15 minutes) to recover cells, and the recovered cells were suspended in a 20 mM Tris buffer solution (Tris-HCl, 1 M NaCl pH 8), disrupted by sonicator, and then the suspension was centrifuged (16000 rpm, 4° C., 60 minutes) to separate β-agarooligosaccharide hydrolase from the supernatant and purify using a HisTrap HP column and a HisTrap Q FF column (GE Healthcare, Piscataway, N.J., USA), which was then observed through 8% SDS-PAGE.

FIG. 3 is an SDS-PAGE image of a purified β-agarooligosaccharide hydrolase. M represents a protein marker, Lane 1 represents a β-agarooligosaccharide hydrolase primarily purified by a HisTrap HP column, and Lane 2 represents the β-agarooligosaccharide hydrolase secondarily purified by a HisTrap Q FF column.

As shown in FIG. 3, the β-agarooligosaccharide hydrolase was found at a position corresponding to about 90 kDa.

<Example 3> Identification of Optimal Reaction Conditions of β-Agarooligosaccharide Hydrolase The optimal conditions consisting only of temperature and pH of a β-agarooligosaccharide hydrolase were identified. Agarotriose (Aglyco, Beijing, China) was used as the substrate, and the results were determined at temperatures of 10, 20, 30, 35, 40, 45, and 50° C. and pH of 4, 5, 6, 7, 8, 9, and 10.

FIG. 4 shows the optimal temperature and pH results of the β-agarooligosaccharide hydrolase of the present invention. FIG. 4A shows the optimal pH of the β-agarooligosaccharide hydrolase with respect to an agarotriose substrate, and FIG. 4B shows the optimal temperature of the β-agarooligosaccharide hydrolase with respect to the agarotriose substrate As shown in FIG. 4, the temperature at which the relative activity for agarotriose reached 50% ranged from about 30 to 40° C., and the pH ranged from 5 to 9.6. The optimal enzyme activity was attained at 35° C. and pH 7.

<Example 4> Determination of Biochemical Activity of Agarooligosaccharide Hydrolase Under the Optimal Conditions β-Agarooligosaccharide hydrolase activity with respect to agarotriose, agaropentaose and agaroheptaose substrates was tested under conditions of 35° C. and pH 7, which were optimal conditions identified in the example 3.

When the changes in the substrate and products with respect to a time of reaction between the β-agarooligosaccharide hydrolase and the agarotriose substrate were observed through HPLC (KS-802 column) and TLC (conditions for the TLC solvent: n-Buthanol:EtOH:Water=3:1:1) analyses, it could be recognized that the β-agarooligosaccharide hydrolase breaks down one molecule of agarooligosaccharide into one molecule of neoagarooligosaccharide and one molecule of D-galactose by hydrolysis (FIG. 5A)

Also, when the changes in the substrate and products with respect to the time of reaction between the β-agarooligosaccharide hydrolase plus α-neoagarobiose hydrolase and the agarotriose substrate were analyzed by HPLC, it could be recognized that 3,6-anhydro-L-galactose and D-galactose were ultimately produced from agarooligosaccharide using the β-agarooligosaccharide hydrolase and α-neoagarobiose hydrolase in combination (FIG. 5B).

FIG. 6 shows the TLC results of β-agarooligosaccharide hydrolase activity of the present invention with respect to agarotriose, agaropentaose, and agaroheptaose substrates. As seen in FIG. 6A, β-agarooligosaccharide hydrolase hydrolyzed agaropentaose and agaroheptaose as well as agarotriose to produce D-galactose, and the ultimate production of 3,6-anhydro-L-galactose and D-galactose was observed when used in combination with β-agarooligosaccharide hydrolase and α-neoagarobiose hydrolase (FIG. 6B).

<Example 5> Comparison of Activity of β-Agarooligosaccharide Hydrolase and *E. Coli*-Derived β-Galactosidase When compared with other β-galactosidases that belong to GH family 2 in terms of activity, the β-agarooligosaccharide hydrolase originated from *Vibrio* sp. EJY3 was found to be an enzyme that belongs to GH family 2 yet shows a new activity different from the previously reported β-galactosidases. The activity of an *E. coli*-derived β-galactosidase (Sigma-Aldrich, 3050 spruce street, USA) was tested with respect to each substrate, and the activity of a β-agarooligosaccharide hydrolase was tested for the same substrates.

FIG. 7 shows the activity results of β-agarooligosaccharide hydrolase with respect to various substrates. Enzyme reactivity was tested with respect to each of lactose, lacto-N-neotetraose, lactulose, 4-β-galactobiose, and α-1,3-β-1,4-galactotriose, and the results reveal that there was no reactivity with respect to any of the substrates.

FIG. 8 shows the results of *E. coli*-derived β-galactosidase hydrolase activity with respect to various substrates. Enzyme reactivity was tested with respect to each of lactose, lacto-N-neotetraose, lactulose, 4-β-galactobiose, and α-1,3-β-1,4-galactotriose, and the already known activity of β-galactosidase was confirmed (FIG. 8A). In addition, enzyme reactivity with respect to each of agarotriose, agaropentaose, and agaroheptaose was tested, and the results confirm that the *E. coli*-derived β-galactosidase cannot hydrolyze agarooligosaccharide (FIG. 8B).

The above results demonstrates that the present invention could improve the product yield and efficiency of agarose saccharification using β-agarooligosaccharide hydrolase, and the schematic view of the saccharification process is as shown in FIG. 9.

INDUSTRIAL APPLICABILITY 3,6-Anhydro-L-galactose and D-galactose of the present invention can be used as a useful material in food, cosmetic, and pharmaceutical fields.

The invention claimed is:

1. A method of saccharifying agarose to produce 3,6-anhydro-L-galactose and D-galactose comprising:
   reacting acid-pretreated agarose with an enzyme mixture of an agarase, a β-agarooligosaccharide hydrolase, and an α-neoagarobiose hydrolase,
   wherein the agarase comprises the amino acid sequence of SEQ ID NO: 3, the β-agarooligosaccharide hydrolase comprises the amino acid sequence of SEQ ID NO: 1, and α-neoagarobiose hydrolase comprises the amino acid sequence of SEQ ID NO: 4.

2. The method of claim 1, wherein the reaction is carried out in a temperature range of 20 to 40° C. under conditions of 0 to 200 rpm for a duration ranging from 30 minutes to 7 days.

3. A method of producing galactose comprising:
   reacting a substrate with a β-agarooligosaccharide hydrolase to produce galactose,
   wherein the substrate is selected from the group consisting of agarotriose, agaropentaose, and agaroheptaose, and
   wherein the β-agarooligosaccharide hydrolase comprises the amino acid sequence of SEQ ID NO: 1.

4. The method of claim 3, wherein the reaction is carried out in a temperature range of 20 to 40° C. and pH range of 5 to 9.6.

5. A method of saccharifying agarose to produce 3,6-anhydro-L-galactose and D-galactose comprising
   allowing an agarase, a β-agarooligosaccharide hydrolase, and an α-neoagarobiose hydrolase to react sequentially with acid-pretreated agarose,
   wherein the agarase comprises the amino acid sequence of SEQ ID NO: 3, the β-agarooligosaccharide hydrolase comprises the amino acid sequence of SEQ ID NO: 1, and α-neoagarobiose hydrolase comprises the amino acid sequence of SEQ ID NO: 4.

6. The method of claim 5, wherein the reaction is carried out in a temperature range of 20 to 40° C. under conditions of 0 to 200 rpm for a duration ranging from 30 minutes to 7 days.

\* \* \* \* \*